(12) United States Patent
Llop

(10) Patent No.: US 11,213,367 B2
(45) Date of Patent: Jan. 4, 2022

(54) DENTAL BONE FOUNDATION GUIDE WITH BUR INSTRUMENT GUIDE FEATURES

(71) Applicant: NATIONAL DENTEX, LLC, Palm Beach Gardens, FL (US)

(72) Inventor: Daniel R. Llop, Cornelius, NC (US)

(73) Assignee: NATIONAL DENTEX, LLC, Jupiter, FL (US)

( * ) Notice: Subject to any disclaimer, the term of this patent is extended or adjusted under 35 U.S.C. 154(b) by 25 days.

(21) Appl. No.: 16/704,349

(22) Filed: Dec. 5, 2019

(65) Prior Publication Data
US 2020/0197126 A1 Jun. 25, 2020

Related U.S. Application Data

(60) Provisional application No. 62/783,286, filed on Dec. 21, 2018.

(51) Int. Cl.
*A61C 1/08* (2006.01)
*A61C 8/00* (2006.01)

(52) U.S. Cl.
CPC .............. *A61C 1/082* (2013.01); *A61C 8/001* (2013.01)

(58) Field of Classification Search
CPC ....... A61C 1/082; A61C 1/084; A61C 8/0089; A61C 8/0048; A61C 8/005; A61C 13/2656; A61C 13/225; A61C 13/10; A61C 13/26; A61B 17/15; A61B 7/151; A61B 17/154; A61B 2017/1602
USPC ..................................................... 606/88, 89
See application file for complete search history.

(56) References Cited

U.S. PATENT DOCUMENTS

| 3,436,826 A * | 4/1969 | Edelman ................ A61C 8/001 433/75 |
| 5,743,916 A * | 4/1998 | Greenberg ............. A61B 17/02 606/102 |
| 8,585,402 B2 * | 11/2013 | Vogel ..................... A61C 1/084 433/72 |
| 8,899,984 B2 | 12/2014 | Llop et al. |
| 9,504,533 B2 | 11/2016 | Groscurth et al. |
| 9,693,834 B2 | 7/2017 | Llop |
| 9,795,458 B2 | 10/2017 | Llop |
| 10,405,945 B2 * | 9/2019 | Llop ...................... A61C 1/084 |

(Continued)

OTHER PUBLICATIONS

U.S. Appl. No. 62/697,549, entitled "Dental Bone Foundation Guide with Palatal or Lingual Side Gap," filed Jul. 13, 2018.

*Primary Examiner* — Jacqueline T Johanas
*Assistant Examiner* — Sharon E Kennedy
(74) *Attorney, Agent, or Firm* — Frost Brown Todd, LLC

(57) ABSTRACT

An apparatus includes a first guide and a second guide. The first guide includes an arcuate horizontal body portion. A rear surface of the horizontal body portion is configured to closely mate with a front-facing bone structure of an alveolar arch of a patient. The second guide includes a body and a coupling member. The body defines a passageway that is configured to receive a bone reducing instrument. The coupling member is configured to mate with the horizontal body portion of the first guide. The body and the coupling member are configured to position the passageway along a second horizontal plane that is parallel with the first horizontal plane. The coupling member is configured to enable the second guide to move relative to the first guide along the second horizontal plane and thereby guide the bone reducing instrument along the second horizontal plane.

19 Claims, 7 Drawing Sheets

(56) References Cited

U.S. PATENT DOCUMENTS

| | | | |
|---|---|---|---|
| 2002/0183760 A1* | 12/2002 | McGovern | A61B 17/1764 606/88 |
| 2003/0236524 A1* | 12/2003 | Squires | A61B 17/142 606/87 |
| 2004/0219478 A1* | 11/2004 | Harter | A61C 1/084 433/75 |
| 2014/0248577 A1* | 9/2014 | Tahmasebi | A61C 1/082 433/75 |
| 2014/0272778 A1 | 9/2014 | Llop | |
| 2015/0010881 A1 | 1/2015 | Llop | |
| 2015/0320430 A1* | 11/2015 | Kehres | A61B 17/15 606/87 |
| 2016/0038255 A1 | 2/2016 | Llop | |
| 2017/0112591 A1 | 4/2017 | Llop | |
| 2017/0112592 A1 | 4/2017 | Groscurth et al. | |
| 2017/0252126 A1 | 9/2017 | Llop | |
| 2018/0235726 A1* | 8/2018 | Zastrow | A61B 17/176 |
| 2020/0015934 A1* | 1/2020 | Llop | A61B 17/176 |
| 2021/0244514 A1* | 8/2021 | Bilodeau | A61C 1/084 |

\* cited by examiner

DENTAL BONE FOUNDATION GUIDE WITH BUR INSTRUMENT GUIDE FEATURES

PRIORITY

This application claims priority to U.S. Provisional Pat. App. No. 62/783,286, entitled "Dental Bone Foundation Guide with Bur Instrument Guide Features," filed Dec. 21, 2018, the disclosure of which is incorporated by reference herein in its entirety.

BACKGROUND

Some patients may develop tooth loss warranting prosthetic replacement. Some instances may warrant a full dental arch restoration. To properly seat a permanent dental prosthetic, it may be necessary to remodel dental bone structures, thereby providing a substantially flat foundation for the prosthetic. After providing a substantially flat foundation, the dental surgeon may drill passageways into the bone in which to secure implants. Once these passageways are formed and the implants are secured therein, the surgeon may secure the prosthetic to the implants, thereby permanently affixing the prosthetic to the patient's bone.

Various forms of hardware may be used to perform the above-described surgical procedure. Examples of such hardware and associated procedures are described in U.S. Pat. No. 8,899,984, entitled "CT-Based, Side-Loading Surgical and Laboratory Dental Implant Guide System and Method," issued Dec. 2, 2014, the disclosure of which is incorporated by reference herein; U.S. Pat. No. 9,504,533, entitled "Endentulous Surgical Guide," issued Nov. 29, 2016, the disclosure of which is incorporated by reference herein; U.S. Pat. No. 9,693,834, entitled "Implant-Based Attachment System for Dental Implant Surgical Guide and Method," issued Jul. 4, 2017, the disclosure of which is incorporated by reference herein; U.S. Pat. No. 9,795,458, entitled "Dental Surgical Implant Guide and Prosthesis Combination and Method of Use," issued Oct. 24, 2017, the disclosure of which is incorporated by reference herein; U.S. Pub. No. 2014/0272778, entitled "Bone Foundation Guide and Method of Use," published Sep. 18, 2014, the disclosure of which is incorporated by reference herein; U.S. Pub. No. 2015/0010881, entitled "Bone Foundation Guide and Method of Use," published Jan. 8, 2015, the disclosure of which is incorporated by reference herein; U.S. Pub. No. 2016/0038255, entitled "Bone Foundation Guide System and Method," published Feb. 11, 2016, the disclosure of which is incorporated by reference herein; U.S. Pub. No. 2017/0112591, entitled "Bone Foundation Guide System and Method," published Apr. 27, 2017, the disclosure of which is incorporated by reference herein; U.S. Pub. No. 2017/0112592, entitled "Method of Using an Endentulous Surgical Guide," published Apr. 27, 2017, the disclosure of which is incorporated by reference herein; and U.S. Pub. No. 2017/0252126, entitled "Bone Foundation Guide System and Method," published Sep. 7, 2017, the disclosure of which is incorporated by reference herein.

While several dental surgical systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc.

should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Bone Foundation Guide

Figure 1:
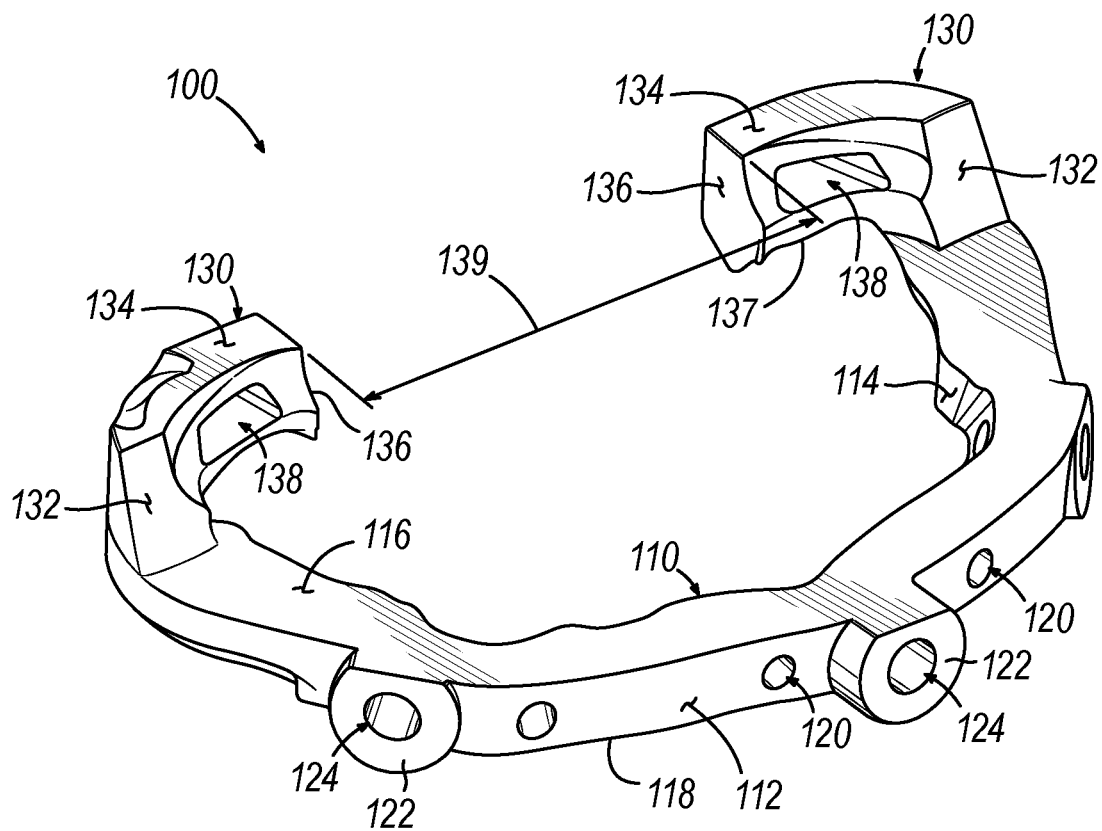
FIG. 1 depicts a perspective view of an exemplary bone foundation guide.
Figure 2:
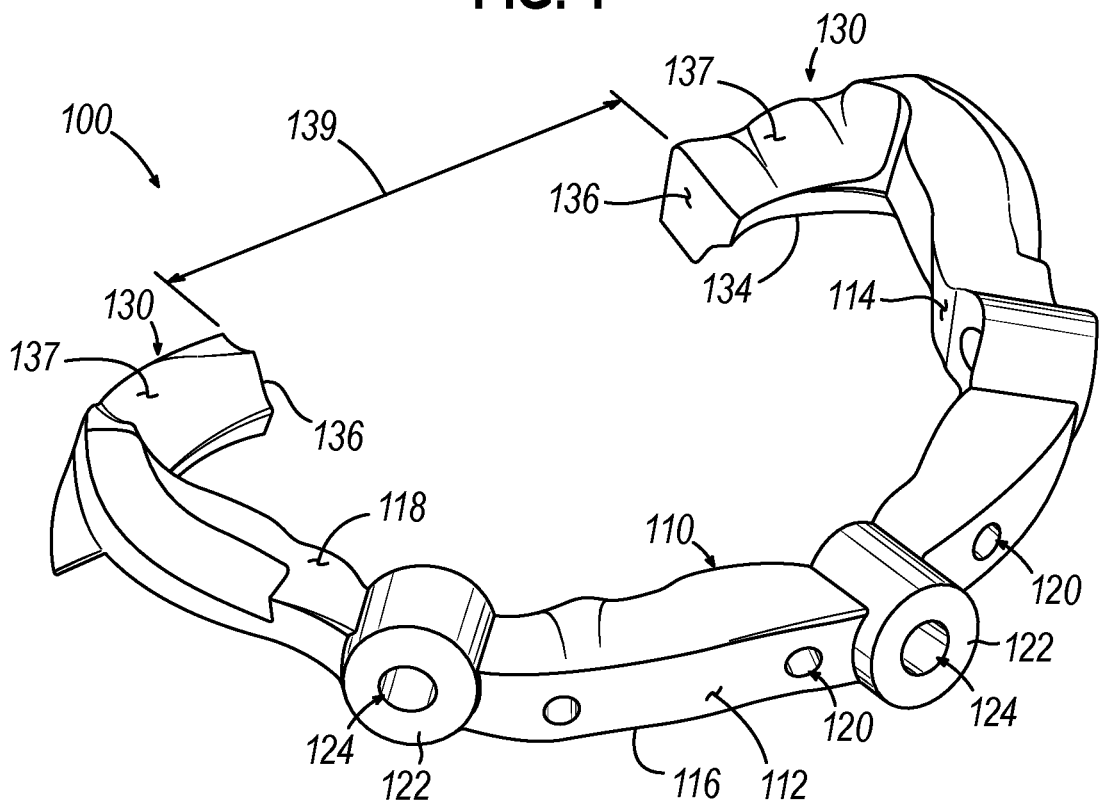
FIG. 2 depicts another perspective view of the bone foundation guide of FIG. 1.
Figure 3:
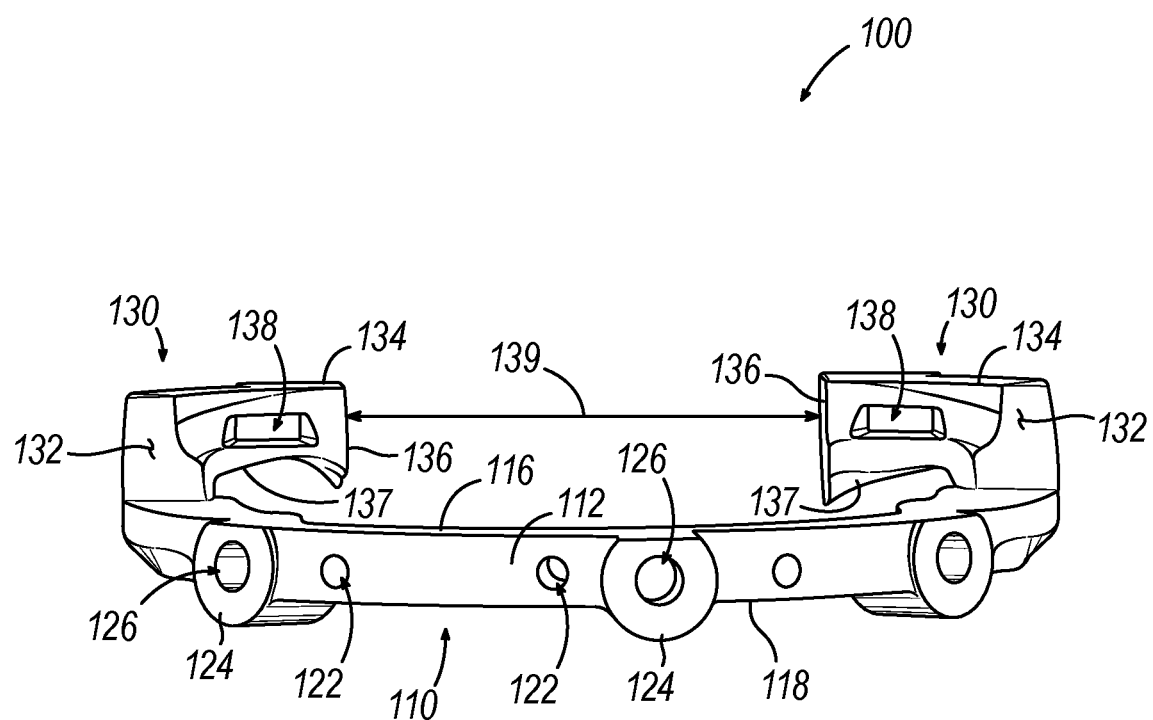
FIG. 3 depicts a front elevation view of the bone foundation guide of FIG. 1.

FIGS. 1-3 show an exemplary bone foundation guide (100), or bone reduction guide, that may be used in combination with other components in a surgical procedure as described below. Bone foundation guide (100) includes a horizontal body portion (110) and a pair of upright body portions (130). Horizontal body portion (110) extends along a horizontal plane and defines an arcuate shape corresponding to an alveolar arch of a patient, as described in greater detail below. Upright body portions (130) are located at each end of the arc defined by horizontal body portion (110). In some versions, bone foundation guide (100) is generated based on a three-dimensional digital model that is created based on a three-dimensional digital model of the patient's oral anatomy. Such a process may be performed in accordance with the teachings of any of the various patent references cited herein; and/or in accordance with the nSequence® Guided Prosthetics® Kit and workflow by National Dentex, LLC of Palm Beach Gardens, Fla.

Horizontal body portion (110) includes a front surface (112), a rear surface (114), an upper surface (116), and a lower surface (118). The terms "upper" and "lower" are being used herein in the exemplary context of bone foundation guide (100) and other devices being mounted to the mandibular alveolar arch. However, as noted below, some versions of bone foundation guide (100) may be mounted to the maxillary alveolar arch, in which cases upper surface (116) would in fact be presented downwardly; and lower source (118) upwardly. Use of the terms "upper" and "lower" should therefore not be read as limiting the alveolar ridge to which bone foundation guide (100) may be secured.

In the present example, rear surface (114) is configured to correspond directly to the configuration of the front-facing surface of the patient's alveolar arch, to thereby provide full surface-to-surface contact along the entirety of rear surface (114) when bone foundation guide (100) is fully seated on the alveolar arch. Rear surface (114) is thus configured to closely mate with a corresponding region of the bone structure of the alveolar arch of the patient. The configuration of rear surface (114) is customized per patient in this example, such that the configuration of rear surface (114) is based upon the anatomical surface geometry embodied in the three-dimensional digital model of the patient's anatomy. Upper surface (116) is substantially flat in this example, to thereby provide a substantially horizontal plane for guidance of an osteotomy bone reduction procedure as described below. In some other versions, upper surface (116) is undulating. In such versions, the undulations of upper surface (116) may be positioned and configured to correspond with positions of prosthetic teeth that will ultimately be installed in the patient's mouth. This may ultimately provide a more natural appearance at the interface between the gumline and the prosthetic teeth.

Horizontal body portion (110) also includes a plurality of passageways (120, 124) extending from front surface (112) to rear surface (114). Passageways (120) are configured to align with corresponding passageways of other devices as will be described in greater detail below. Passageways (124) are configured to receive fasteners to secure bone foundation guide (100) to the alveolar ridge of a patient. By way of example only, bone foundation guide (100) may be secured to the alveolar ridge via pins, screws, or other features disposed in passageways (124). Passageways (124) are surrounded by cylindraceous stand-off features (122) in the present example. Stand-off features (122) are configured to reinforce the structural integrity of horizontal body portion (110) in the regions around passageways (124).

Each upright body portion (130) includes a vertically extending front surface (132), a horizontally extending upper surface (134), a vertically extending inner surface (136), and a lower surface (137). A slot (138) is formed through each upright body portion (130). In the present example, surfaces (132, 134, 136) are generally flat. A gap (139) extends laterally between inner surfaces (136). Lower surface (137) is configured to correspond directly to the configuration of an upwardly facing surface of the patient's alveolar arch (or the downwardly facing surface when bone foundation guide (100) is mounted to the maxillary alveolar arch), to thereby provide full surface-to-surface contact along the entirety of lower surface (137) when bone foundation guide (100) is fully seated on the alveolar arch. Lower surface (137) is thus configured to closely mate with the bone structure of a corresponding region of the alveolar ridge of the patient. The configuration of lower surface (137) is customized per patient in this example, such that the configuration of lower surface (137) is based upon the anatomical surface geometry embodied in the three-dimensional digital model of the patient's anatomy.

As best seen in FIG. 3, each lower surface (137) is positioned vertically higher than the horizontal plane of upper surface (116) in this example. Similarly, slots (138) are also positioned vertically higher than the horizontal plane of upper surface (116) in this example.

Those skilled in the art will recognize that bone foundation guide (100) of this example has only one single horizontal body portion (110) in this example. The single horizontal body portion (110) is configured to fit only on the buccal side of a patient's alveolar arch in this example—regardless of whether it is the mandibular alveolar arch or the maxillary alveolar arch—as will be described in greater detail below. Unlike conventional bone foundation guides, there is no additional horizontal body portion (110) that fits on the palatal or lingual side of the alveolar arch. This may provide in a reduced cost to manufacture bone foundation guide (100) due to the reduction of materials. Omitting a horizontal body portion (110) that fits on the palatal or lingual side of the alveolar arch may also reduce the amount of gum (G) tissue that needs to be moved away from bone (B) during installation of bone foundation guide (100) on the alveolar arch. The omission of a horizontal body portion (110) that fits on the palatal or lingual side of the alveolar arch may also improve the accuracy of seating of bone foundation guide (100) on the alveolar arch because the palatal or lingual tissue does not interfere with or otherwise contact horizontal body portion. In addition, the absence of a horizontal body portion (110) that fits on the palatal or lingual side of the alveolar arch may also improve visualization of anatomical structures such as arteries attached to gingiva, etc. The omission of a horizontal body portion (110) that fits on the palatal or lingual side of the alveolar arch may also assist in keeping the implant sites irrigated and cool. Other potential advantages of the configuration of bone foundation guide (100) of the present example will be apparent to those skilled in the art in view of the teachings herein.

By way of example only, bone foundation guide (100) may be formed using rapid prototyping equipment (e.g., 3D printing or other additive manufacturing, etc.), based on a three-dimensional digital model as noted above. By way of further example only, bone foundation guide (100) may be formed of plastic, metal, other materials, and combinations thereof. Various suitable ways in which bone foundation guide (100) may be formed will be apparent to those skilled in the art in view of the teachings herein.

II. Exemplary Bone Reduction Procedure

Figure 4A:
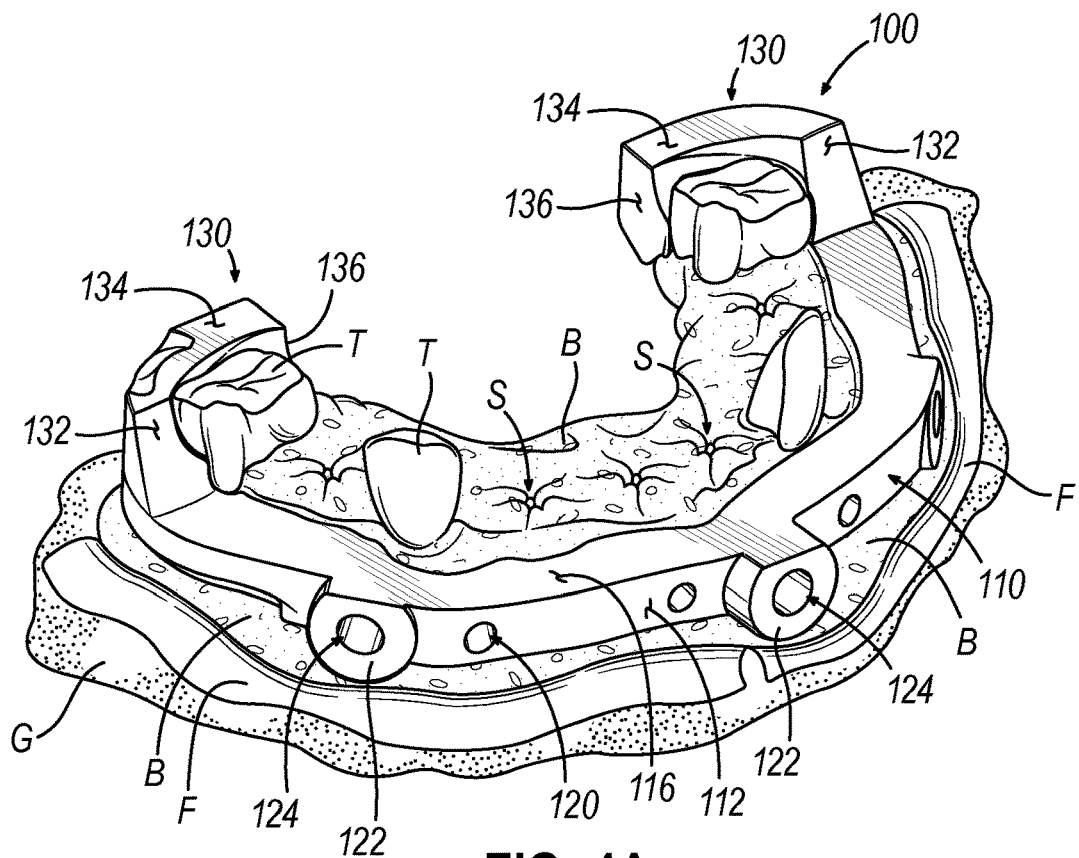
FIG. 4A depicts a perspective view of the bone foundation guide of FIG. 1 mounted to an alveolar ridge of a patient, before a bone reduction procedure.
Figure 4B:
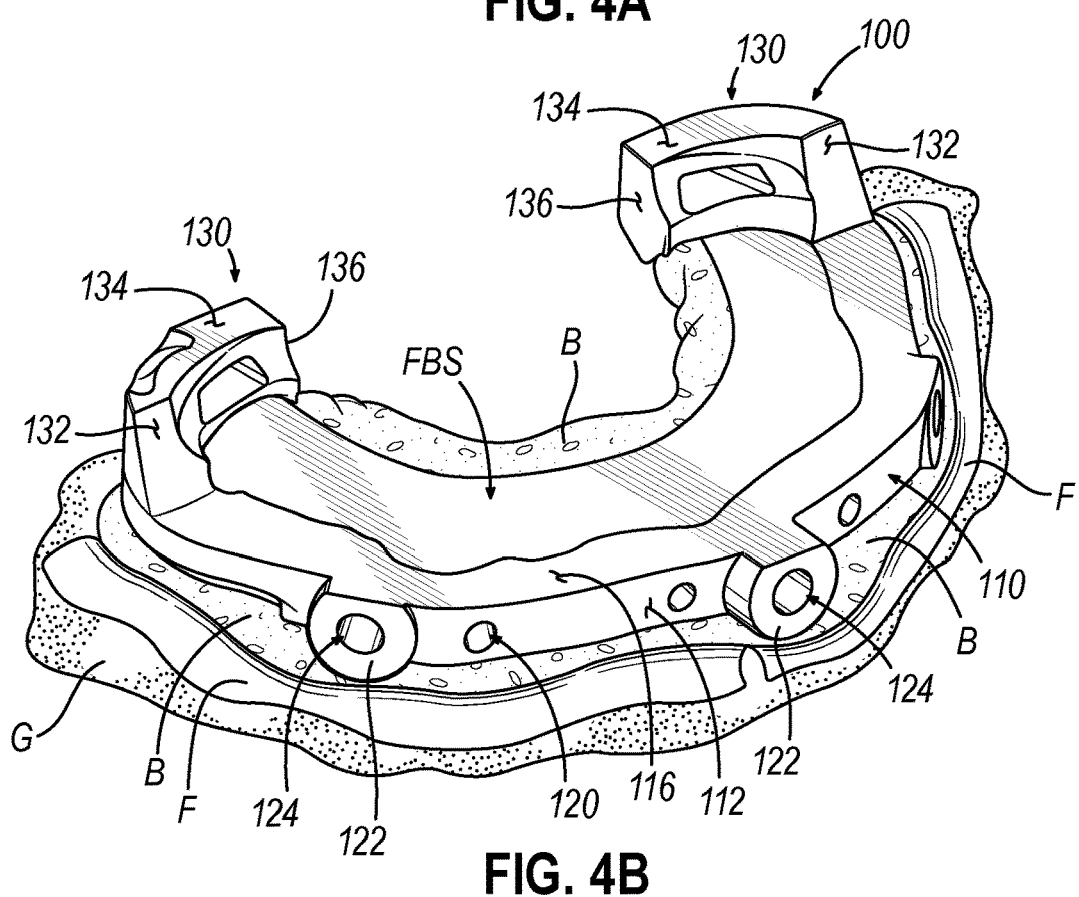
FIG. 4B depicts a perspective view of the bone foundation guide of FIG. 1 mounted to an alveolar ridge of a patient, after a bone reduction procedure.
Figure 5:
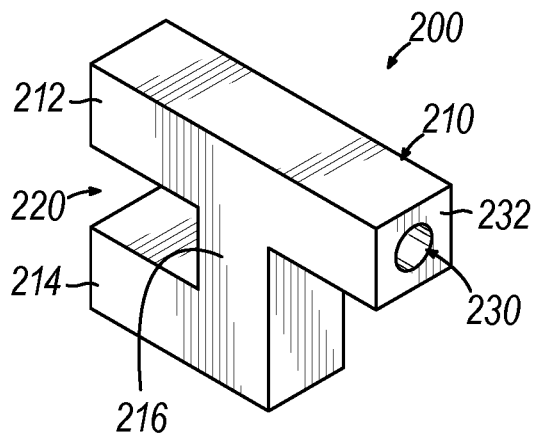
FIG. 5 depicts a perspective view of an exemplary bur guide that may be mounted to the bone foundation guide of FIG. 1.
Figure 6:
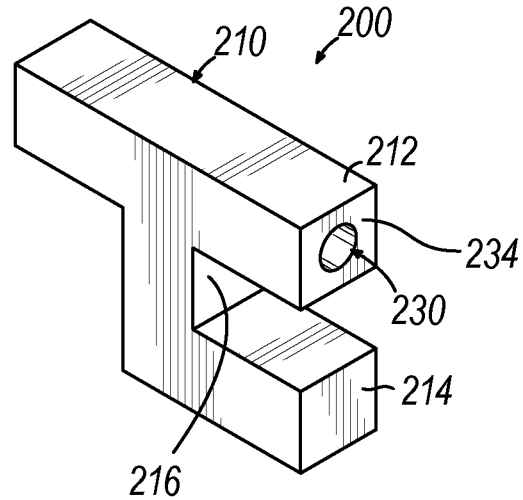
FIG. 6 depicts another perspective view of the bur guide of FIG. 5.

FIGS. 4A-4B show different stages of an exemplary surgical procedure in which bone foundation guide (100) is used to guide reduction of bone on an alveolar arch of a patient. As shown in FIG. 4A, bone foundation guide (100) is positioned over an alveolar arch of a patient. In the present example, the alveolar arch is the mandibular alveolar arch, though the same procedure and similar equipment may be used on the maxillary alveolar arch. The only difference would be the bone foundation guide (100) having a customized configuration to fit on the maxillary alveolar arch.

As shown, before bone foundation guide (100) is installed, the surgeon incises the gum (G) along the ridge of the alveolar arch and peels the gum (G) away, leaving flaps (F) to reveal bone (B). In the present example, bone foundation guide (100) rests entirely on bone (B), without being supported by any gum (G) tissue. As is also shown in FIG. 4A, the patient in this case is missing several teeth, leaving behind sockets (S), with a few teeth (T) remaining. In order to fixedly secure bone foundation guide (100) to the bone (B), the surgeon may drive pins, screws, or other fastener devices through passageways (124). Such fastener devices may be removable to facilitate removal of bone foundation guide (100) after the procedure is complete. With bone foundation guide (100) being installed on the bone (B), horizontal body portion (110) extends only along the buccal side of the alveolar arch. No horizontally extending portion of bone foundation guide (100) wraps along the lingual (or palatal) side of the alveolar arch. Lower surfaces (137) of upright body portions (130) rest on the upper ridge of the alveolar arch, thereby supplementing the structural support provided by the fastener devices that are disposed in passageways (124) and bone (B).

After securing bone foundation guide (100) to bone as shown in FIG. 4A, the surgeon may remove the remaining teeth (T) using any suitable techniques. In some cases, the surgeon may then secure a strut assembly (not shown) to bone foundation guide (100). The strut assembly may include representations of teeth that will be incorporated into a prosthetic that will ultimately be mounted to the alveolar arch. By way of example only, the strut assembly may be configured and operable in accordance with at least some of the teachings of U.S. Pat. App. No. 62/697,549, entitled "Dental Bone Foundation Guide with Palatal or Lingual Side Gap," filed Jul. 13, 2018, the disclosure of which is incorporated by reference herein.

To secure the strut assembly to bone foundation guide (100), the operator may insert tabs of the strut assembly into corresponding slots (138) of bone foundation guide (100). The operator may also insert pins, screws, or other fastener devices through openings (120) and corresponding openings of the strut assembly to further secure the strut assembly to bone foundation guide (100). With the strut assembly coupled with bone foundation guide (100), the surgeon may establish a state of occlusion between the representative teeth of the strut assembly and the teeth of the opposing alveolar ridge of the patient. This may be done as a preview to confirm that the teeth of the planned prosthetic will be an appropriate fit for the patient, since the teeth of the strut assembly match the placement and configuration of the teeth of the planned prosthetic. After confirming the appropriate fit, the surgeon may remove the strut assembly from bone foundation guide (100). Of course, this use of a strut assembly is merely optional. Bone foundation guide (100) may be used in various procedures that do not include use of a strut assembly.

Next, the physician may perform an osteotomy or bone reduction procedure on the alveolar ridge. This may include using a conventional bur or other cutting instrument to remove all portions of the bone (B) that protrudes above the upper surface (116) of bone foundation guide (100). In some instances, the physician may add material to bone (B). Such added material may be formed in part by bone material that has just been removed from the alveolar ridge. In either case, the end result of such procedures may look similar to the state shown in FIG. 4B, in which a flush bone surface (FBS) is established. This flush bone surface (FBS) is substantially coplanar with the upper surface (116) of bone foundation guide (100), such that bone foundation guide (100) serves as a bone reduction guide. To achieve this flush bone surface (FBS), the surgeon may use upper surface (116) to provide a visual cue, and in some cases structural support, for the instrumentation that is used to remove the bone (B) protruding above upper surface (116) and/or for the instrumentation that is used to add material to the bone (B) to achieve a flat, planar flush bone surface (FBS). Bone foundation guide (100) may thus provide structural and/or visual guidance for instrumentation during a bone reduction procedure. Bone foundation guide (100) may also provide structural and/or visual guidance for a bone augmentation procedure. The degree of bone reduction and bone augmentation that is required may vary patient to patient, depending on the extent to which bone reduction and bone augmentation is required along the alveolar arch in order to achieve a flat, planar flush bone surface (FBS) that is flush with upper surface (116).

After completing the bone reduction (and perhaps bone augmentation) procedure, the surgeon may couple a surgical guide (not shown) with bone foundation guide (100). By way of example only, the strut assembly may be configured and operable in accordance with at least some of the teachings of U.S. Pat. App. No. 62/697,549, entitled "Dental Bone Foundation Guide with Palatal or Lingual Side Gap," filed Jul. 13, 2018, the disclosure of which is incorporated by reference herein. To secure the surgical guide to bone foundation guide (100), the operator may insert tabs of the surgical guide into corresponding slots (138) of bone foundation guide (100). The operator may also insert pins, screws, or other fastener devices through openings (120) and corresponding openings of the surgical guide to further secure the strut assembly to bone foundation guide (100). After the surgical guide and bone foundation guide (100) are coupled together, the surgeon may insert a drill or other instrument successively in guide passageways of the surgical guide to form openings in bone (B) to receive implants. The surgeon may then insert the implants and associated installation instrumentation through the passageways of the surgical guide to install the implants. After the implants are installed, the surgeon may install abutments on the implants, again via the passageways of the surgical guide. After the abutments are installed, the surgeon may remove the surgical guide and bone foundation guide (100) from the alveolar arch.

In some versions of the procedure, before or after the implants and abutments are installed, the surgeon may also position a tissue-spacing gasket about the implants and abutments and then secure a temporary prosthetic to the abutments, with the tissue-spacing gasket being configured to mimic the thickness of the gum (G) tissue forming flaps (F). Such a tissue-spacing gasket and temporary prosthetic may be configured and operable in accordance with the teachings of any of the various patent references cited herein. The surgeon may eventually remove the tissue-spacing gasket and temporary prosthetic, bring the flaps (F) back over the alveolar ridge and stitch the gum (G) tissue around the abutments, and then secure the final prosthetic to the abutments. Again, this may be performed in accordance with the teachings of any of the various patent references cited herein.

The foregoing example of how bone foundation guide (100) may be used in a medical procedure is merely illustrative. Bone foundation guide (100) may be used in various other kinds of medical procedures and in combination with various other kinds of devices. Other suitable ways in which bone foundation guide (100) may be used will be apparent to those skilled in the art in view of the teachings herein.

III. Exemplary Bur Guide

As noted above, bone foundation guide (100) may serve two separate purposes when mounted to a patient's alveolar ridge—serving as a bone reduction guide (and perhaps a bone augmentation guide); and serving as a structural foundation upon which other devices (e.g., strut assembly, surgical guide, etc.) are supported. When bone foundation guide (100) is used as a bone reduction guide for a bur instrument or other bone cutting instrument, it may be difficult for some surgeon to quickly and accurately achieve a flush bone surface (FBS) that is substantially coplanar with the upper surface (116) of bone foundation guide (100). It may therefore be desirable to provide an adapter for bone foundation guide (100) that serves as a guide for a bur instrument or other bone cutting instrument, thereby making it easier for a surgeon to quickly and accurately achieve a flush bone surface (FBS) that is substantially coplanar with the upper surface (116) of bone foundation guide (100). Examples of such guide adapters are described in greater detail below.

FIGS. 5-9 show an exemplary bur guide (200) that may be used to assist in guiding a bur instrument (300) in relation to bone foundation guide (100) and in relation to the bone (B) of the alveolar ridge of the patient. Bur guide (200) of this example comprises a body (210) with a first horizontal portion (212), a second horizontal portion (214), and a vertical portion (216). Both horizontal portions (212, 214) extend distally in relation to vertical portion (216), defining a notch (220) therebetween. First horizontal portion (212) also extends proximally in relation to vertical portion (216) in this example. First horizontal portion (212) defines a passageway (230) extending from a proximal face (232) of first horizontal portion (212) to a distal face (234) of first horizontal portion.

Figure 7:
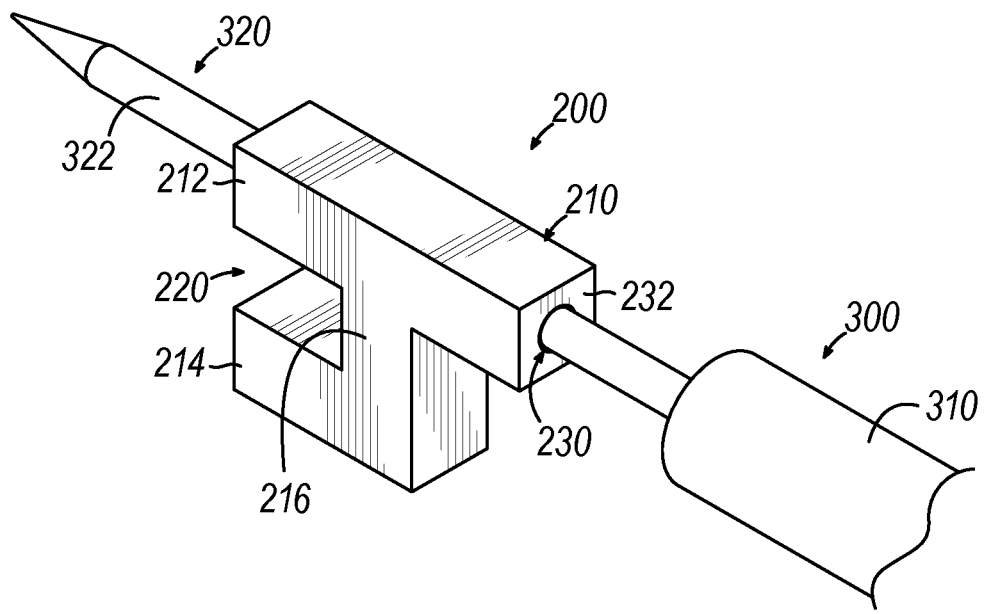
FIG. 7 depicts a perspective view of a shaft of a bur instrument disposed in the bur guide of FIG. 5.

As shown in FIG. 7, passageway (230) is sized to receive a shaft (322) of a bur bit (320) of a bur instrument (300), such that an operator grasping a handle assembly (310) (schematically represented in FIG. 7) may insert bur bit (320) through passageway (230) at proximal face (232), with bur bit (320) eventually exiting at distal face (234). In the present example, a mechanism in handle assembly (310) is operable to cause bur bit (320) to rotate about the longitudinal axis of shaft (322), and this rotary movement of bur bit (320) is operable to cut bone (B). In some versions, bur bit (320) is configured such that the entire length of shaft (322) extending through passageway (230) is smooth; while only the portion of shaft (322) that is distal to passageway (230) includes features that are configured to cut bone.

Passageway (230) of the present example has a circular cross-sectional profile with an inner diameter that is sized just slightly larger than the outer diameter of shaft (322)—large enough to permit shaft (322) to rotate within passageway (230) but small enough to provide at least some degree of structural support to shaft (322). In some versions, a bushing, ferrule, and/or other component is positioned in passageway (230) to facilitate rotation of shaft (322) in passageway (230). As yet another merely illustrative variation, passageway (230) may have a cross-sectional profile that is rectangular or otherwise non-circular. In such variations, bur guide (200) may be configured to cooperate with a bone cutting instrument that utilizes a saw or other reciprocating cutting element to cut bone (B). Other suitable variations of passageway (230) and bone cutting instruments that may be inserted through passageway (230) will be apparent to those skilled in the art in view of the teachings herein.

Figure 8:
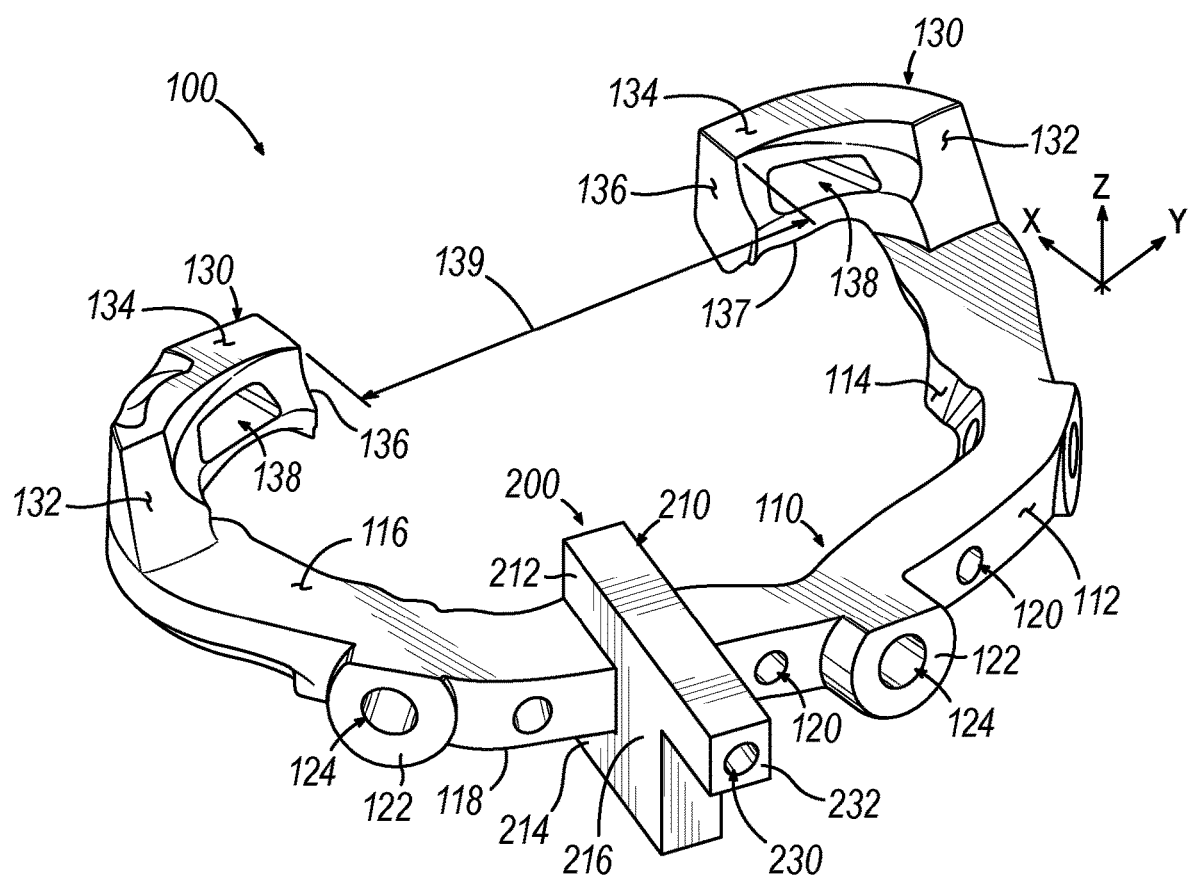
FIG. 8 depicts a perspective view of the bur guide of FIG. 5 mounted to the bone foundation guide of FIG. 1.

As shown in FIG. 8, bur guide (200) may be coupled with bone foundation guide (100). In particular, notch (220) of bur guide (220) is configured to receive horizontal body portion (110). The fit between notch (220) and horizontal body portion (110) allows bur guide (200) to slide along the arch of horizontal body portion (110) along the x-y plane; while preventing movement of bur guide (200) along the z-axis. In this example, the x-y plane is parallel with upper surface (116) of horizontal body portion (110). During use of bur guide (200), bur guide (200) may slide along the arch of horizontal body portion (110) along the x-y plane in the regions between cylindraceous stand-off features (122). Bur guide (200) may also slide along the arch of horizontal body portion (110) along the x-y plane in the regions between cylindraceous stand-off features (122) and upright body portions (130). In some variations of bone foundation guide (100), stand-off features (122) are reconfigured to allow bur guide (200) to slide freely along the entire length of horizontal body portion (110), from one upright body portion (130) to the other upright body portion (130).

Figure 9:
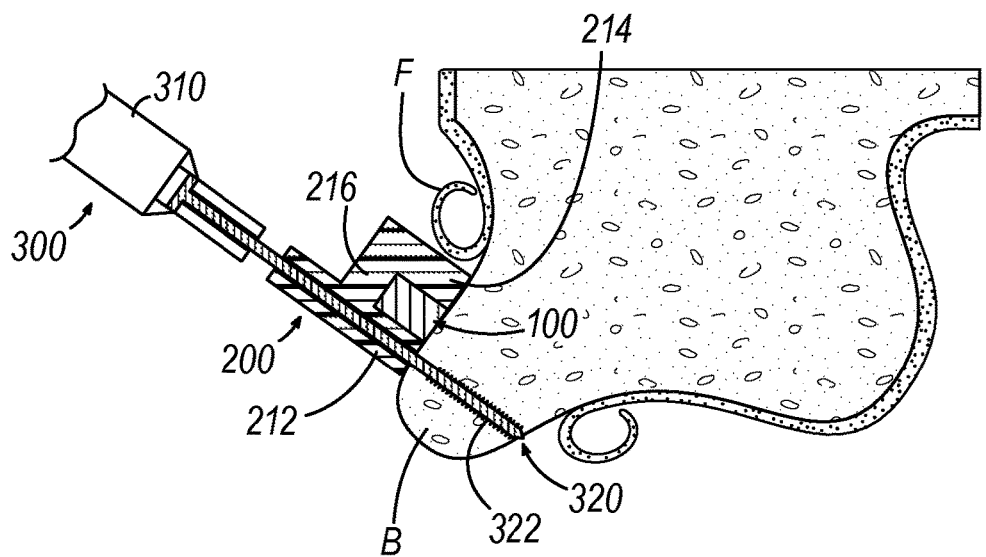
FIG. 9 depicts a cross-sectional view of the bur guide of FIG. 5 mounted to the bone foundation guide of FIG. 1, with the bone foundation guide mounted to an alveolar ridge of a patient, and with the shaft of a bur instrument disposed in the bur guide and removing bone from the alveolar ridge.
Figure 10:
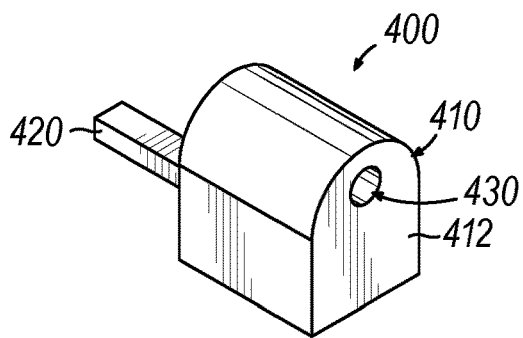
FIG. 10 depicts a perspective view of another exemplary bur guide.
Figure 11:
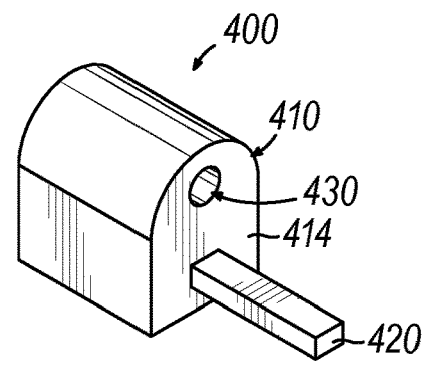
FIG. 11 depicts another perspective view of the bur guide of FIG. 10.

FIG. 9 shows shaft (322) of bur bit (320) disposed in passageway (230) while bone foundation guide (100) is mounted to an alveolar arch of a patient. As shown, bur bit (320) cuts bone (B) as guided by bur guide (200). While shaft (322) is disposed in passageway (230) and bur bit (320) is activated to rotate, the operator may slide bur instrument (300) and bur guide (200) together along horizontal body portion (110), along the x-y plane, thereby cutting bone (B) along an x-y plane. The operator may still provide substantial structural support to bur instrument (300) by maintaining a grip on handle assembly (310); while bur guide (200) provides some support to bur bit (320) to facilitate steady, sweeping movement of bur but (320) along an x-y plane. In some instances, the operator may need to either remove bur bit (320) from bur guide (200) or slightly pivot bur guide (200) about the z-axis in order for bur bit (320) to reach bone (B) in the regions of the alveolar arch corresponding to stand-off features (122).

Upon completion of the sweeping movement of bur instrument (300) and bur guide (200) along the x-y plane, the final result may be a flat, planar bone surface like the flush bone surface (FBS) shown in FIG. 4B and described above. In some versions of bur guide (200), passageway (230) is configured to position bur bit (320) just slightly above upper surface (116) of bone foundation guide (100), such that the flush bone surface (FBS) is coplanar with upper surface (116) of bone foundation guide (100). In some other versions of bur guide (200), passageway (230) is configured to position bur bit (320) at a height where the final cut surface of bone (B) is slightly higher than upper surface (116) yet extends along an x-y plane that parallel with the plane of upper surface (116). In such versions, the strut assembly, surgical guide, or other device(s) that is/are used in conjunction with bone foundation guide (100) may be configured to account for the slight offset between the final cut surface of bone (B) and upper surface (116). As yet another merely illustrative variation, where upper surface (116) is undulating instead of being flat as described above, bur guide (200) may traverse the undulations and the final cut surface of bone (B) may therefore also be undulating to complement the undulations of upper surface (116). As noted above, this ultimately provide a more natural appearance at the interface between the gumline and prosthetic teeth that are ultimately secured to the bone (B).

FIGS. 10-11 and 14-15 show another exemplary bur guide (500) that may be used to assist in guiding a bur instrument (300) in relation to a slightly different bone foundation guide (600) and in relation to the bone (B) of the alveolar ridge of the patient. Bur guide (400) of this example comprises a body (410) with a passageway (430) extending between a proximal face (412) and distal face (414) of body (410). A prong (420) projects distally from distal face (414) of body (410). Passageway (430) is sized to receive a shaft (322) of a bur instrument (300), such that an operator grasping a handle assembly (310) of bur instrument (300) may insert bur bit (320) through passageway (430) at proximal face (412), with bur bit (320) eventually exiting at distal face (414). In some versions, bur bit (320) is configured such that the entire length of shaft (322) extending through passageway (430) is smooth; while only the portion of shaft (322) that is distal to passageway (430) includes features that are configured to cut bone.

Passageway (430) of the present example has a circular cross-sectional profile with an inner diameter that is sized just slightly larger than the outer diameter of shaft (322)—large enough to permit shaft (322) to rotate within passageway (430) but small enough to provide at least some degree of structural support to shaft (322). In some versions, a bushing, ferrule, and/or other component is positioned in passageway (430) to facilitate rotation of shaft (322) in passageway (430). As yet another merely illustrative variation, passageway (430) may have a cross-sectional profile that is rectangular or otherwise non-circular. In such variations, bur guide (400) may be configured to cooperate with a bone cutting instrument that utilizes a saw or other reciprocating cutting element to cut bone (B). Other suitable variations of passageway (430) and bone cutting instruments that may be inserted through passageway (430) will be apparent to those skilled in the art in view of the teachings herein.

Figure 12:
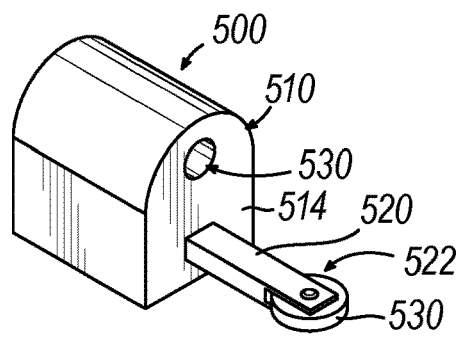
FIG. 12 depicts a perspective view of an exemplary variation of the bur guide of FIG. 10.

Prong (420) is configured to fit in a slot (650) of bone foundation guide (600) and thereby support body (410) as bur guide (400) slides along the arch of horizontal body portion (610) of bone foundation guide (600) as described in greater detail below. While prong (420) is shown as having a squared distal end in this example, other versions may provide a rounded distal end of prong (420). FIG. 12 shows an exemplary variation of bur guide (400). In particular, FIG. 12 shows a bur guide (500) that is substantially identical to bur guide (400), with bur guide (500) having a body (510) and a passageway (530) extending from a proximal face to a distal face (514) of body (510). However, unlike bur guide (400), bur guide (500) of this example includes a prong (520) with a wheel (530) coupled with a yoke (522) at the distal end of prong (520). Wheel (530) is configured to spin freely in yoke (522) about an axis that is perpendicular to prong (520). In this example, the rotation axis for wheel (530) is parallel to the z-axis shown in FIG. 14, such that the rotation axis is perpendicular to the x-y plane associated with upper surface (616) of bone foundation guide (600). The presence and free rotatability of wheel (530) may facilitate sweeping movement of bur guide (500) along the arch of horizontal body portion (610) of bone foundation guide (600) as described in greater detail below.

Figure 13:
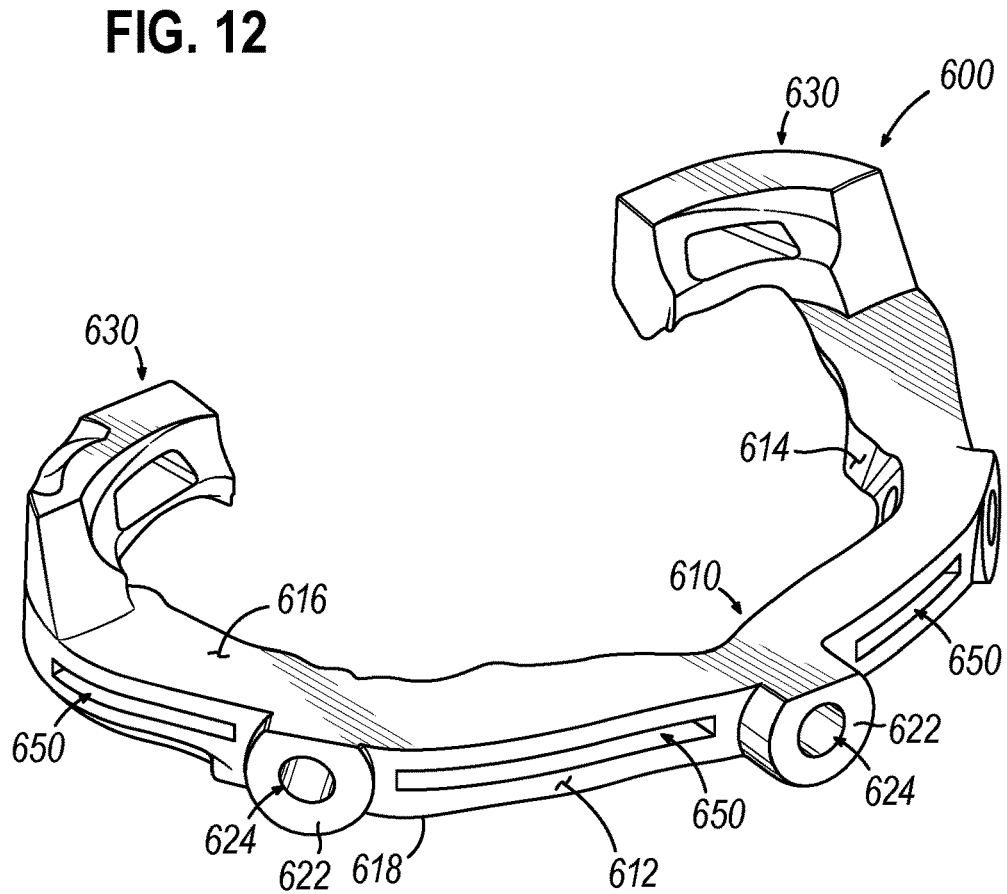
FIG. 13 depicts a perspective view of an exemplary alternative bone foundation guide that is configured to couple with the bur guide of FIG. 10 or the bur guide of FIG. 11.
Figure 14:
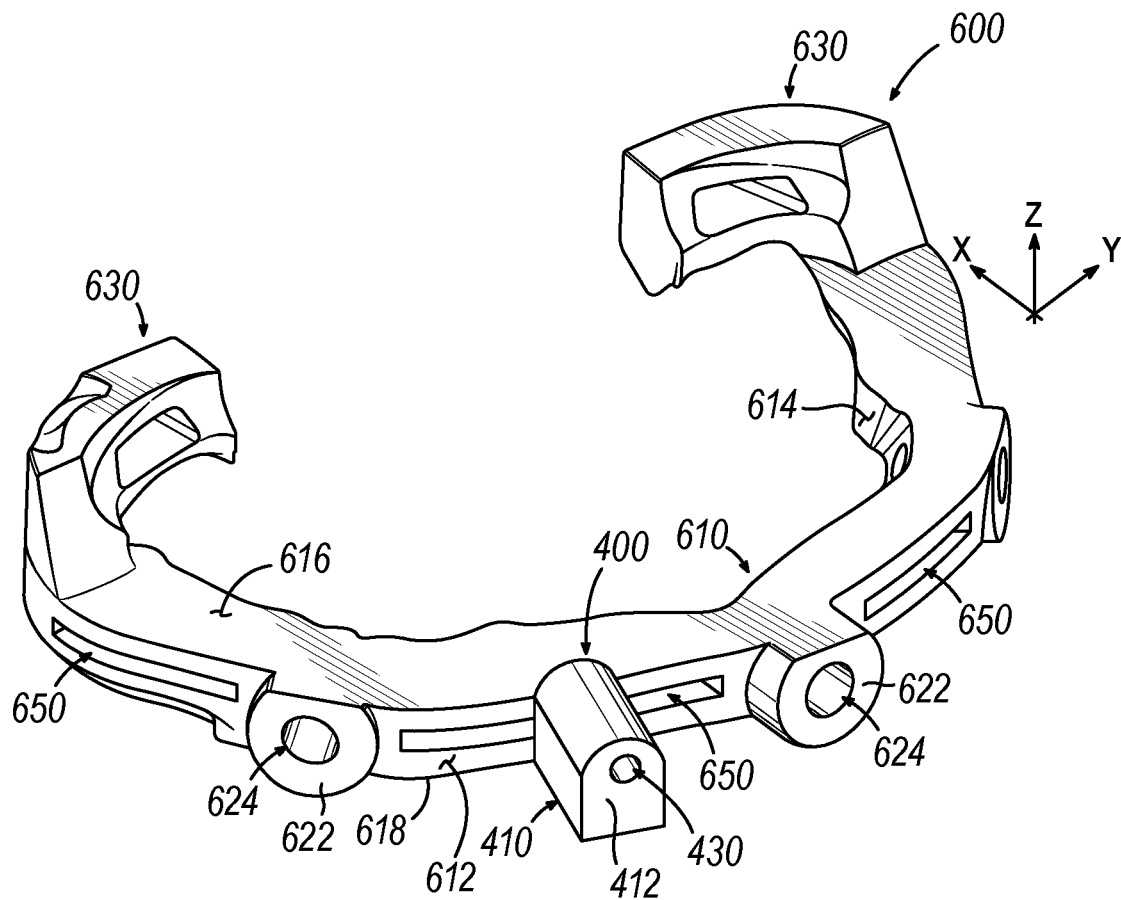
FIG. 14 depicts a perspective view of the bur guide of FIG. 10 mounted to the bone foundation guide of FIG. 13.
Figure 15:
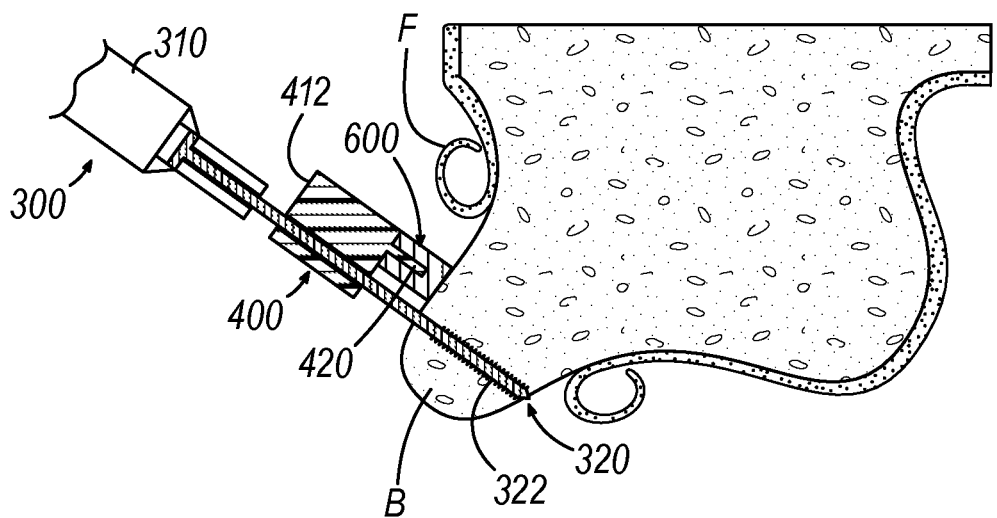
FIG. 15 depicts a cross-sectional view of the bur guide of FIG. 10 mounted to the bone foundation guide of FIG. 13, with the bone foundation guide mounted to an alveolar ridge of a patient, and with the shaft of a bur instrument disposed in the bur guide and removing bone from the alveolar ridge.

FIGS. 13-15 show bone foundation guide (600) that is particularly suited for use with bur guide (500). Bone foundation guide (600) is substantially identical to bone foundation guide (100) in that bone foundation guide (600) of this example includes horizontal body portion (610) with a front surface (612), a rear surface (614), and an upper surface (616); stand-off features (622) with corresponding passageways (624); and upright body portions (630) at each end of horizontal body portion (610).

Unlike bone foundation guide (100), bone foundation guide (600) of this example includes four slots (650) formed in front surface (612) of horizontal body portion (610). Slots (650) extend along an x-y plane that is parallel with the x-y plane defined by upper surface (616). Two of the slots (650) extend between stand-off features (622). The other two slots (650) each extend between a stand-off feature (622) and corresponding upright body portion (630). In some other versions, stand-off features (622) are omitted. In some such versions, bone foundation guide (600) only includes one single slot (650) that extends continuously from one upright body portion (630) to the other upright body portion (630).

While upper surface (616) is substantially flat in this example, upper surface (616) may instead be undulating as described above in the context of upper surface (116). Regardless of whether upper surface (616) is undulating, slots (650) may define undulating paths to thereby provide undulating movement (along the y-z plane) as prong (420, 520) traverses slots (650). Such undulations may provide undulating movement of bur bit (320), which may in turn provide an undulating cut surface of bone (B), which may ultimately provide a more natural appearance at the interface between the gumline and the prosthetic teeth.

As shown in FIG. 14, bur guide (400) may be coupled with bone foundation guide (600). In particular, each slot (650) of bone foundation guide (600) is configured to receive prong (420) of bone foundation guide (600). The fit between prong (420) and slot (650) allows bur guide (400) to slide along the arch of horizontal body portion (610) along the x-y plane; while preventing movement of bur guide (400) along the z-axis. In this example, the x-y plane is parallel with upper surface (616) of horizontal body portion (610). During use of bur guide (400), bur guide (400) may slide along the arch of horizontal body portion (610) along the x-y plane in the regions between cylindraceous stand-off features (622). Bur guide (400) may also slide along the arch of horizontal body portion (610) along the x-y plane in the regions between cylindraceous stand-off features (622) and upright body portions (630).

FIG. 15 shows shaft (322) of bur bit (320) disposed in passageway (430) while bone foundation guide (600) is mounted to an alveolar arch of a patient. As shown, bur bit (320) cuts bone (B) as guided by bur guide (400). While shaft (322) is disposed in passageway (430) and bur bit (320) is activated to rotate, the operator may slide bur instrument (300) and bur guide (400) together along horizontal body portion (610), along the x-y plane, thereby cutting bone (B) along an x-y plane. The operator may still provide substantial structural support to bur instrument (300) by maintaining a grip on handle assembly (310); while bur guide (400) provides some support to bur bit (320) to facilitate steady, sweeping movement of bur but (320) along an x-y plane. In some instances, the operator may need to either remove bur bit (320) from bur guide (400) or slightly pivot bur guide (400) about the z-axis in order for bur bit (320) to reach bone (B) in the regions of the alveolar arch corresponding to stand-off features (622).

Upon completion of the sweeping movement of bur instrument (300) and bur guide (400) along the x-y plane, the final result may be a flat, planar bone surface like the flush bone surface (FBS) shown in FIG. 4B and described above. In some versions of bur guide (400), passageway (430) is configured to position bur bit (320) just slightly above upper surface (616) of bone foundation guide (600), such that the flush bone surface (FBS) is coplanar with upper surface (616) of bone foundation guide (600). In some other versions of bur guide (400), passageway (430) is configured to position bur bit (320) at a height where the final cut surface of bone (B) is slightly higher than upper surface (616) yet extends along an x-y plane that parallel with the plane of upper surface (616). In such versions, the strut assembly, surgical guide, or other device(s) that is/are used in conjunction with bone foundation guide (600) may be configured to account for the slight offset between the final cut surface of bone (B) and upper surface (616).

While the foregoing examples include one bur guide (200) that relies in part on a horizontal portion (214) under a lower surface (118) of a bone foundation guide (100) to provide structural stability to bur guide (200) along the z-axis, and another bur guide (400, 500) that relies in part on a distally extending prong (420, 520) to provide structural stability to bur guide (400, 500) along the z-axis, some variations may include both such features. For instance, bur guide (400, 500) may be modified to include a horizontal member like horizontal portion (214) that engages lower surface (618) of bone foundation guide (600). Such an additional horizontal member may cooperate with prong (420, 520) to provide additional stability to bur guide (400, 500) along the z-axis. Other features that may be incorporated into a bur guide (200, 400, 500) to provide structural stability along the z-axis will be apparent to those skilled in the art in view of the teachings herein.

As another merely illustrative variation, bur guide (200, 400, 500) may include one or more lateral openings in fluid communication with passageway (230, 430, 530). Such openings may be configured to enable irrigation fluid (e.g., water, etc.) to reach passageway (230, 430, 530), to thereby provide liquid cooling at the interface between shaft (322) and passageway (230, 430, 530).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a first guide comprising a horizontal body portion, wherein the horizontal body portion has an arcuate configuration, wherein the horizontal body portion includes: (i) a first horizontal surface, wherein the first horizontal surface is flat and defines a first horizontal plane, (ii) a front surface, (iii) a rear surface, wherein the rear surface is configured to closely mate with a front-facing bone structure of an alveolar arch of a patient, and (iv) a second horizontal surface, wherein the front and rear surfaces extend between the first and second horizontal surfaces; and (b) a second guide comprising: (i) a body defining a passageway, wherein the passageway is configured to receive a bone reducing instrument, and (ii) a coupling member configured to mate with the horizontal body portion of the first guide, wherein the body and the coupling member are configured to position the passageway along a second horizontal plane that is parallel with the first horizontal plane, wherein the coupling member is configured to enable the second guide to move relative to the first guide along the second horizontal plane and thereby guide the bone reducing instrument along the second horizontal plane.

Example 2

The apparatus of Example 1, wherein the first guide further comprises a pair of upright portions, each upright portion being positioned at a respective end of the horizontal body portion.

Example 3

The apparatus of any one or more of Examples 1 through 2, wherein the body of the second guide comprises: (A) a first horizontal portion, (B) a second horizontal portion, and (C) a vertical portion extending between the first and second horizontal portion.

Example 4

The apparatus of Example 3, wherein the first horizontal portion extends distally in relation to the vertical portion, wherein the second horizontal portion extends distally in relation to the vertical portion.

Example 5

The apparatus of Example 4, wherein the body of the second guide defines a notch, wherein the notch is defined by the vertical portion and the regions of the first and second horizontal portions extending distally in relation to the vertical portion.

Example 6

The apparatus of Example 5, wherein the notch is configured to receive the horizontal body portion of the first guide, such that the vertical portion and the regions of the first and second horizontal portions extending distally in relation to the vertical portion together define the coupling member.

Example 7

The apparatus of any one or more of Examples 4 through 6, wherein the first horizontal portion further extends proximally in relation to the vertical portion.

Example 8

The apparatus of Example 7, wherein the passageway extends through the first horizontal portion.

Example 9

The apparatus of any one or more of Examples 1 through 8, wherein the passageway has a circular cross-section.

Example 10

The apparatus of any one or more of Examples 1 through 9, the second guide further comprising a bushing or ferrule in the passageway.

Example 11

The apparatus of any one or more of Examples 1 through 10, further comprising a bur instrument having a bur shaft, the bur shaft being configured to fit in the passageway, the bur shaft having a distal portion configured to reduce bone.

Example 12

The apparatus of any one or more of Examples 1 through 11, the coupling member comprising a prong extending distally from the body.

Example 13

The apparatus of Example 12, the front surface of the horizontal body portion defining at least one slot, wherein the at least one slot is configured to receive the prong of the coupling member.

Example 14

The apparatus of Example 13, wherein the at least one slot is configured to allow the second guide to slide along at least a portion of the arcuate configuration of the first guide.

Example 15

The apparatus of any one or more of Examples 12 through 14, wherein the prong includes a wheel located at a distal end of the prong.

Example 16

A method of reducing bone on an alveolar ridge of a patient, the method comprising: (a) securing a first guide to the alveolar ridge of the patient, wherein the first guide has an arcuate configuration complementing an arcuate configuration of the alveolar ridge, wherein the alveolar ridge includes bone protruding past a first horizontal surface of the first guide, the first horizontal surface extending along a first horizontal plane; (b) securing a second guide to the first guide, wherein the second guide defines a passageway; (c) inserting a working element of a bone reduction instrument through the passageway, wherein the passageway is configured to position the working element along a second horizontal plane that is parallel with the first horizontal plane; (d) activating the bone reduction instrument while the working element is disposed in the passageway; and (e) moving the second guide along the first guide, thereby moving the working element of the bone reduction instrument along the second horizontal plane while the bone reduction instrument is activated, wherein the working element reduces the bone that is protruding past the first horizontal surface of the first guide.

Example 17

The method of Example 16, wherein the act of securing the second guide to the first guide comprises positioning a horizontal body portion of the first guide in a notch defined by the second guide.

Example 18

The method of any one or more of Examples 16 through 17, wherein the act of securing the second guide to the first guide comprises positioning a prong of the second guide in a slot defined by a horizontal body portion of the first guide.

Example 19

The method of any one or more of Examples 16 through 18, wherein the working element comprises a bur bit.

Example 20

The method of Example 19, wherein activating the bone reduction instrument comprises rotating the bur bit.

Example 21

The method of any one or more of Examples 16 through 20, further comprising moving gum tissue away from bone of the alveolar ridge to expose the bone of the alveolar ridge, wherein the act of moving the gum tissue is performed before the act of securing the first guide to the alveolar ridge.

Example 22

The method of Example 21, wherein the first guide is secured only to the exposed bone, such that the first guide is not secured to any gum tissue.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
   (a) a first guide comprising a horizontal body portion, wherein the horizontal body portion has an arcuate configuration, wherein the horizontal body portion includes:
      (i) a first horizontal surface, wherein the first horizontal surface is flat and defines a first horizontal plane,
      (ii) a front surface,
      (iii) a rear surface, wherein the rear surface is configured to closely mate with a front-facing bone structure of an alveolar arch of a patient, and
      (iv) a second horizontal surface,
      wherein the front and rear surfaces extend between the first and second horizontal surfaces; and
   (b) a second guide comprising:
      a body defining a passageway, wherein the passageway is configured to receive a bone reducing instrument, and
      (ii) a coupling member vertically offset relative to the passageway of the body, wherein the coupling member is configured to mate with the horizontal body portion of the first guide to thereby restrict vertical movement of the second guide relative to the first guide while allowing the second guide to translate along a path defined by the horizontal body,
      wherein the body and the coupling member are configured to position the passageway along a second horizontal plane that is parallel with the first horizontal plane,
      wherein the coupling member is configured to enable the second guide to move relative to the first guide along the second horizontal plane and thereby guide the bone reducing instrument along the second horizontal plane.

2. The apparatus of claim 1, wherein the first guide further comprises a pair of upright portions, each upright portion being positioned at a respective end of the horizontal body portion.

3. The apparatus of claim 1, wherein the body of the second guide comprises:
   (A) a first horizontal portion,
   (B) a second horizontal portion, and
   (C) a vertical portion extending between the first and second horizontal portion.

4. The apparatus of claim 3, wherein the first horizontal portion extends distally in relation to the vertical portion, wherein the second horizontal portion extends distally in relation to the vertical portion.

5. The apparatus of claim 4, wherein the body of the second guide defines a notch, wherein the notch is defined by the vertical portion and the regions of the first and second horizontal portions extending distally in relation to the vertical portion.

6. The apparatus of claim 5, wherein the notch is configured to receive the horizontal body portion of the first guide, such that the vertical portion and the regions of the first and second horizontal portions extending distally in relation to the vertical portion together define the coupling member.

7. The apparatus of claim 4, wherein the first horizontal portion further extends proximally in relation to the vertical portion.

8. The apparatus of claim 7, wherein the passageway extends through the first horizontal portion.

9. The apparatus of claim 1, wherein the passageway has a circular cross-section.

10. The apparatus of claim 1, further comprising a bur instrument having a bur shaft, the bur shaft being configured to fit in the passageway, the bur shaft having a distal portion configured to reduce bone.

11. The apparatus of claim 1, the coupling member comprising a prong extending distally from the body.

12. The apparatus of claim 11, the front surface of the horizontal body portion defining at least one slot, wherein the at least one slot is configured to receive the prong of the coupling member.

13. The apparatus of claim 12, wherein the at least one slot is configured to allow the second guide to slide along at least a portion of the arcuate configuration of the first guide.

14. The apparatus of claim 11, wherein the prong includes a wheel located at a distal end of the prong.

15. An apparatus comprising:
(a) a first guide comprising a horizontal body portion, wherein the horizontal body portion has an arcuate configuration, wherein the horizontal body portion includes:
   (i) a first horizontal surface, wherein the first horizontal surface is flat and defines a first horizontal plane,
   (ii) a front surface,
   (iii) a rear surface, wherein the rear surface is configured to closely mate with a front-facing bone structure of an alveolar arch of a patient, and
   (iv) a second horizontal surface,
   wherein the front and rear surfaces extend between the first and second horizontal surfaces; and
(b) a second guide comprising:
   a body defining a passageway, wherein the passageway is configured to receive a bone reducing instrument, wherein the body comprises:
      (A) a first horizontal portion, wherein the passageway extends through the first horizontal portion,
      (B) a second horizontal portion, and
      (C) a vertical portion extending between the first and second horizontal portion,
   (ii) a coupling member configured to mate with the horizontal body portion of the first guide,
   wherein the body and the coupling member are configured to position the passageway along a second horizontal plane that is parallel with the first horizontal plane,
   wherein the coupling member is configured to enable the second guide to move relative to the first guide along the second horizontal plane and thereby guide the bone reducing instrument along the second horizontal plane.

16. An apparatus comprising:
(a) a first guide comprising a horizontal body portion, wherein the horizontal body portion has an arcuate configuration, wherein the horizontal body portion includes:
   (i) a first horizontal surface, wherein the first horizontal surface is flat and defines a first horizontal plane,
   (ii) a front surface,
   (iii) a rear surface, wherein the rear surface is configured to closely mate with a front-facing bone structure of an alveolar arch of a patient, and
   (iv) a second horizontal surface,
   wherein the front and rear surfaces extend between the first and second horizontal surfaces; and
(b) a second guide comprising:
   (i) a body defining a passageway, wherein the passageway is configured to receive a bone reducing instrument, and
   (ii) a coupling member configured to mate with the horizontal body portion of the first guide, wherein the coupling member comprises a prong and a wheel, both of which extend distally from the body,
   wherein the body and the coupling member are configured to position the passageway along a second horizontal plane that is parallel with the first horizontal plane,
   wherein the coupling member is configured to enable the second guide to move relative to the first guide along the second horizontal plane and thereby guide the bone reducing instrument along the second horizontal plane.

17. The apparatus of claim 16, wherein the wheel is rotatably coupled to the prong via a yoke.

18. The apparatus of claim 16, wherein the wheel is coupled to a distal end of the prong.

19. The apparatus of claim 18, wherein the first guide defines a slot dimensioned to slidably receive the wheel and the prong.

* * * * *